United States Patent
Chen et al.

(10) Patent No.: US 10,145,977 B2
(45) Date of Patent: Dec. 4, 2018

(54) METHOD FOR POSITIONING TARGET IN THREE-DIMENSIONAL CT IMAGE AND SECURITY CHECK SYSTEM

(71) Applicant: NUCTECH COMPANY LIMITED, Beijing (CN)

(72) Inventors: Zhiqiang Chen, Beijing (CN); Li Zhang, Beijing (CN); Shuo Wang, Beijing (CN); Yunda Sun, Beijing (CN); Qingping Huang, Beijing (CN); Zhi Tang, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 93 days.

(21) Appl. No.: 15/300,668

(22) PCT Filed: Dec. 15, 2015

(86) PCT No.: PCT/CN2015/097378
§ 371 (c)(1),
(2) Date: Sep. 29, 2016

(87) PCT Pub. No.: WO2016/095798
PCT Pub. Date: Jun. 23, 2016

(65) Prior Publication Data
US 2017/0176631 A1    Jun. 22, 2017

(30) Foreign Application Priority Data
Dec. 18, 2014 (CN) .......................... 2014 1 0795840

(51) Int. Cl.
*G01V 5/00* (2006.01)
*G01N 23/046* (2018.01)
*G06T 11/00* (2006.01)

(52) U.S. Cl.
CPC .......... *G01V 5/005* (2013.01); *G01N 23/046* (2013.01); *G01V 5/0058* (2013.01);
(Continued)

(58) Field of Classification Search
CPC .... G01V 5/005; G01V 5/0058; G01V 5/0041; G01N 23/045; G01N 2223/401; G01N 2223/419; G01N 2223/643
See application file for complete search history.

(56) References Cited

U.S. PATENT DOCUMENTS

| 6,721,387 B1 | 4/2004 | Naidu et al. |
| 9,058,658 B2 | 6/2015 | Li et al. |

(Continued)

FOREIGN PATENT DOCUMENTS

| CN | 101592579 | 12/2009 |
| CN | 102222352 | 10/2011 |

(Continued)

OTHER PUBLICATIONS

Office Action as issued in Chinese Patent Application No. 201410795840.1, dated Jan. 12, 2018.
(Continued)

*Primary Examiner* — Ping Hsieh
(74) *Attorney, Agent, or Firm* — Pillsbury Winthrop Shaw Pittman LLP

(57) ABSTRACT

A method for positioning a target in a three-dimensional CT image and a security check system. The method includes: displaying a three-dimensional CT image; receiving a selection by a user of at least one area of the three-dimensional CT image at a first viewing angle to generate a first three-dimensional description; receiving a selection by the user of at least one area of the three-dimensional CT image at a second viewing angle to generate a second three-dimensional description, wherein an angle between the first view-
(Continued)

ing angle and the second viewing angle is within a predetermined range and the first three-dimensional description and the second three-dimensional description are related to a size, a location, and/or a physical property of a target at corresponding viewing angles; and determining the target in the three-dimensional CT image based on the first three-dimensional description and the second three-dimensional description.

18 Claims, 2 Drawing Sheets

(52) U.S. Cl.
CPC ...... *G06T 11/008* (2013.01); *G01N 2223/401* (2013.01); *G01N 2223/419* (2013.01); *G01N 2223/643* (2013.01); *G01V 5/0041* (2013.01)

(56) References Cited

U.S. PATENT DOCUMENTS

| | | | |
|---|---|---|---|
| 2008/0043917 A1* | 2/2008 | Oreper | G01V 5/0025 378/116 |
| 2008/0123895 A1 | 5/2008 | Gable et al. | |
| 2009/0079738 A1 | 3/2009 | Liao | |
| 2011/0254845 A1* | 10/2011 | Oikawa | G06T 15/08 345/427 |
| 2014/0093152 A1 | 4/2014 | Li et al. | |

FOREIGN PATENT DOCUMENTS

| | | |
|---|---|---|
| CN | 102573638 A | 7/2012 |
| CN | 103713329 A | 4/2014 |
| EP | 2 713 340 | 4/2014 |
| EP | 2960869 A2 | 12/2015 |
| WO | 2010/119690 | 10/2010 |
| WO | 2011/046511 | 4/2011 |

OTHER PUBLICATIONS

Extended European Search Report cited in related European Patent Application No. EP 15869305.1 dated Sep. 7, 2017.
International Search Report and Written Opinion dated Feb. 24, 2016 in corresponding International Patent Application No. PCT/CN2015/097378.

\* cited by examiner

METHOD FOR POSITIONING TARGET IN THREE-DIMENSIONAL CT IMAGE AND SECURITY CHECK SYSTEM

This application is a U.S. National Phase Application of International Patent Application No. PCT/CN2015/097378, filed on Dec. 15, 2015, which claims priority to Chinese Patent Application No. 201410795840.1, filed on Dec. 18, 2014.

TECHNICAL FIELD

The present application relates to the field of security checking, and in particular, to a method for positioning a target in a three-dimensional CT (Computerized Tomographic) image and a security check system.

BACKGROUND

A multi-energy X-ray security check system is a new type of security check system developed based on a mono-energy X-ray security check system. It can provide not only shape and content of an object to be inspected but also information about equivalent atomic number for the object to be inspected, to determine whether the object to be inspected is organic or inorganic, which can be displayed on a color monitor with different colors to facilitate a human operator in identification.

During an image identification process, if a suspected object is found, a human operator for identifying the suspected object in the image is required to mark the suspected object with an input device, such as a mouse. For an item machine system of a DR (Digital Radiographic) type, the principle for marking a suspected object on a two-dimensional DR image is simple and there are many proven solutions. For a security check system of a CT type, there is still a problem to be solved that how to mark a suspected object on a three-dimensional CT image in a quick and accurate manner.

SUMMARY

In view of one or more technical problems in the prior art, the present disclosure proposes a method for positioning a target in a three-dimensional CT image and a security check system which may facilitate users in marking a suspected object in a CT image in a quick manner.

In an aspect of the present disclosure, a method for positioning a target in a three-dimensional CT image is proposed, comprising steps of: displaying a three-dimensional CT image; receiving a selection by a user of at least one area of the three-dimensional CT image at a first viewing angle to generate a first three-dimensional description; receiving a selection by the user of at least one area of the three-dimensional CT image at a second viewing angle to generate a second three-dimensional description, wherein the angle between the first viewing angle and the second viewing angle is in a predetermined range and the first three-dimensional description and the second three-dimensional description are related to at least one of dimensions, positions, or physical attributes of the target at the corresponding viewing angle; and determining the target in the three-dimensional CT image based on the first three-dimensional description and the second three-dimensional description.

According to some embodiments, the step of generating the first three-dimensional description comprises:

acquiring a front plane depth map and a rear plane depth map at the first viewing angle, searching in the front plane depth map and the rear plane depth map based on the area selected by the user at the first viewing angle, respectively, to generate a first bounding box/data subset as the first three-dimensional description;

wherein the step of generating the second three-dimensional description comprises:

acquiring a three-dimensional drawing result at the second viewing angle by using the first generated bounding box/data subset as the drawing range, and acquiring a front plane depth map and a rear plane depth map at the second viewing angle, searching in the front plane depth map and the rear plane depth map based on the area selected by the user at the second viewing angle, respectively, to generate a second bounding box/data subset as the second three-dimensional description;

wherein the step of determining the target in the three-dimensional CT image comprises:

performing an intersection operation on the first bounding box/data subset and the second bounding box/data subset in an image space to determine the target.

According to some embodiments, the step of acquiring the front plane depth map and the rear plane depth map comprises:

performing a depth test in a scenario rendering process and recording the minimal depth value to acquire a front plane depth map; and performing a depth test in the scenario rendering process and recording the maximal depth value to acquire a rear plane depth map.

According to some embodiments, both of the first bounding box/data subset and the second bounding box/data subset are bounding boxes/data subsets in any arbitrary direction.

According to some embodiments, the marked area of the three-dimensional space is merged into and displayed within the CT data.

According to some embodiments, the predetermined range is specifically a range from 45 degrees to 135 degrees.

In another aspect of the present disclosure, a security check CT system is proposed, comprising: a CT scanning device configured to acquire inspection data for an object to be inspected; a memory configured to store the inspection data; a display device configured to display a three-dimensional CT image for the object to be inspected; an input device configured to input a selection by a user of at least one area of the three-dimensional CT image at a first viewing angle, and to input a selection by the user of at least one area of the three-dimensional CT image at a second viewing angle, wherein the angle between the first viewing angle and the second viewing angle is in a predetermined range; and a data processor configured to generate a first three-dimensional description based on the selection at the first viewing angle, generate a second three-dimensional description based on the selection at the second viewing angle, and determine the target in the three-dimensional CT image based on the first three-dimensional description and the second three-dimensional description, wherein the first three-dimensional description and the second three-dimensional description are related to at least one of the dimensions, positions or physical attributes of the target at corresponding viewing angles.

According to some embodiments, the data processor is configured to:

acquire a front plane depth map and a rear plane depth map at the first viewing angle, search in the front plane depth map and the rear plane depth map based on the area selected by the user at the first viewing angle, respectively, to generate a first bounding box/data subset as the first three-dimensional description;

acquire a three-dimensional drawing result at the second viewing angle by using the first generated bounding box/data subset as the drawing range, and acquire a front plane depth map and a rear plane depth map at the second viewing angle, search in the front plane depth map and the rear plane depth map based on the area selected by the user at the second viewing angle, respectively, to generate a second bounding box/data subset as the second three-dimensional description; and perform an intersection operation on the first bounding box/data subset and the second bounding box/data subset in an image space to determine the target.

According to some embodiments, the data processor is configured to:

perform a depth test in a scenario rendering process and record the minimal depth value to acquire a front plane depth map; and perform a depth test in the scenario rendering process and record the maximal depth value to acquire a rear plane depth map.

With the above technical solutions, the user may be facilitated in marking a suspected object in a CT image in a quick manner.

BRIEF DESCRIPTION OF THE DRAWINGS

To understand the present disclosure in a better way, a detailed description of the present disclosure will be given with reference to the following drawings, in which.

DETAILED DESCRIPTION

Specific embodiments of the present disclosure will be described in detail below and please note that the embodiments described herein are used for the purpose of exemplification rather than limitation of the present disclosure. Hereinafter, to provide a thorough understanding of the present disclosure, numerous specific details are set forth. However, it would be obvious for one ordinarily skilled in the art that the present disclosure can be practiced without these specific details. In other examples, known structures, materials, or methods are not described in detail to avoid any possible obfuscation of the present disclosure.

Throughout the specification, the reference to "an embodiment", "the embodiment", "an example", or "the example" is meant that a specific feature, structure, or feature described with reference to this embodiment or example is contained by at least one embodiment of the present disclosure. Therefore, the phrases "in an embodiment", "in the embodiment", "an example", or "the example" throughout the specification is not necessarily intended to refer to a same embodiment or example. Further, specific features, structures, or characteristics may be combined into one or more embodiments or examples in any suitable combination and/or sub-combination. Further, it is appreciated by one ordinarily skilled in the art that the term "and/or" used herein comprises any and all combinations of one or more related items that are listed.

With regard to the problem of the prior art that a target object cannot be marked quickly, the embodiments of the present disclosure propose a method for positioning an object in a three-dimensional CT image. First, a three-dimensional CT image for an object to be inspected is displayed on a display. Next, a selection of at least one area of the three-dimensional CT image at a first viewing angle is received from a user by an input device 65, such as a mouse, to generate a first three-dimensional description. After that, a selection of at least one area of the three-dimensional CT image at a second viewing angle is received from the user, to generate a second three-dimensional description. The angle between the first viewing angle and the second viewing angle is in a predetermined range and the first three-dimensional description and the second three-dimensional description are related to at least one of dimensions, positions, or physical attributes of the target at the corresponding viewing angle. Finally, the target in the three-dimensional CT image is determined based on the first three-dimensional description and the second three-dimensional description. With the above technical solutions, the user may be facilitated in marking a suspected object in a CT image in a quick manner.

Figure 1:
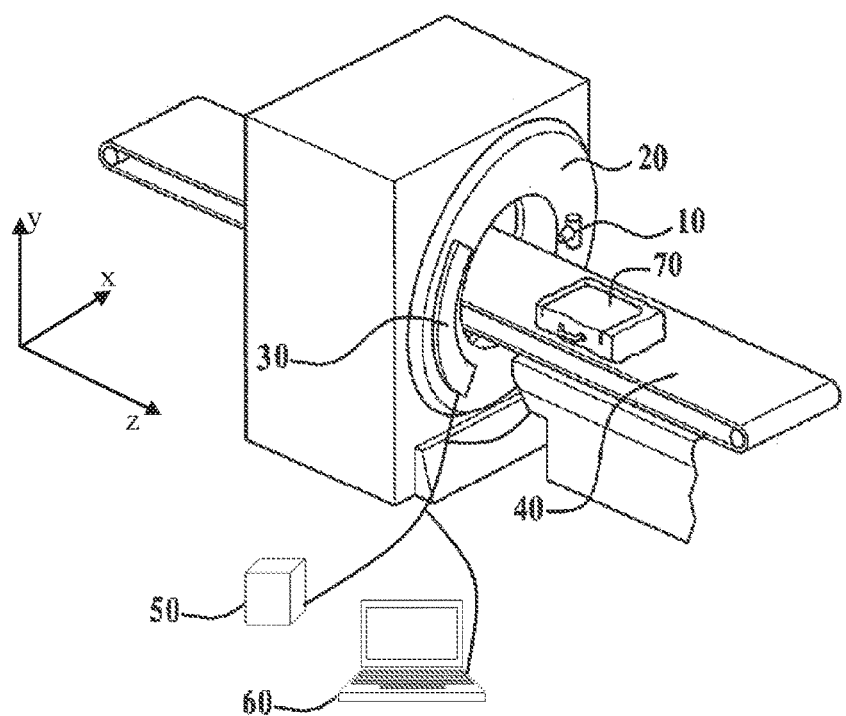
FIG. 1 is a diagram showing the structure of a security check CT system according to an embodiment of the present disclosure.

FIG. 1 is a diagram showing the structure of a CT system according to an embodiment of the present disclosure. As shown in FIG. 1, a CT device according to this embodiment comprises: a rack 20, a bearing mechanism 40, a controller 50, a computer data processor 60, or the like. The rack 20 comprises a ray source 10 configured to emit X-ray for inspection, such as a X-ray machine, and a detection and sampling apparatus 30. The bearing mechanism 40 bears a luggage to be inspected 70 to pass through the scanning area of the rack 20 between the ray source 10 and the detection and sampling apparatus 30, while the rack 20 rotates about the travelling direction of the luggage to be inspected 70 such that the rays emitted from the ray source 10 are able to penetrate through the luggage to be inspected 70 and a CT scan is performed on the luggage to be inspected 70.

The detection and sampling apparatus 30 is, for example, a detector-and-data-sampler with an integrated modular structure, such as a flat panel detector, for detecting rays transmitted through the object to be inspected such that analog signals are acquired and converted into digital signals, thereby outputting projection data of the luggage to be inspected 70 with respect to X-ray. The controller 50 is used for controlling various parts of the whole system to operate synchronously. The computer data processor 60 is used for processing the data sampled by the data sampler, processing and reconstructing the data, and outputting the result.

As shown in FIG. 1, the ray source 10 is located on a side of the object to be inspected, and the detection and sampling apparatus 30 comprising a detector and a data sampler is located on the other side of the luggage to be inspected 70 to acquire multi-angle projection data for the luggage to be inspected 70. The data sampler comprises a data amplification shaping circuit which may operate in a (current) integration manner or a pulse (counting) manner. A data output cable of the detection and sampling apparatus 30 is coupled to the controller 50 and the computer data processor 60, and stores the sampled data into the computer data processor 60 based on a trigger command.

Figure 2:
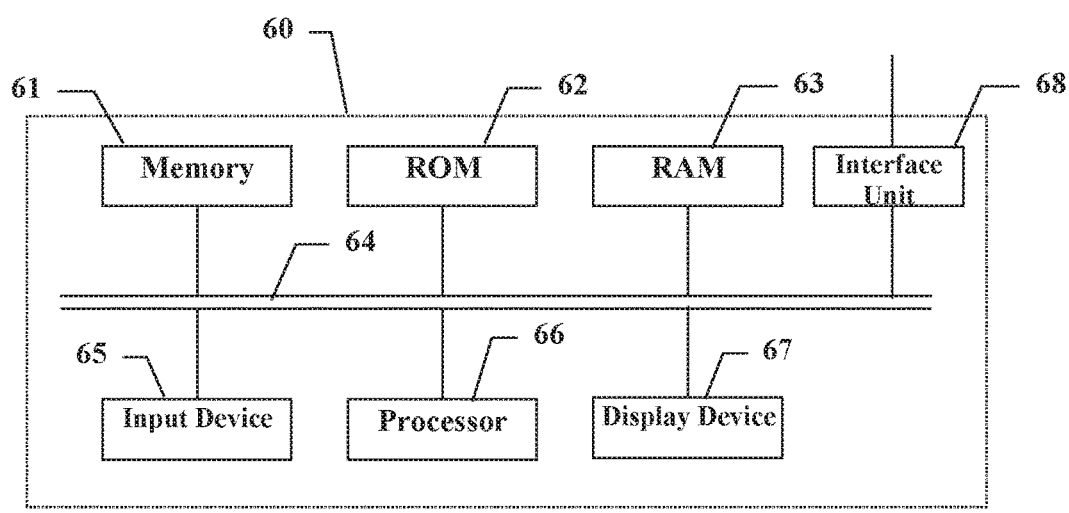
FIG. 2 is a block diagram showing the structure of the computer data processor as shown in FIG. 1.

FIG. 2 is a block diagram showing the structure of the computer data processor 60 as shown in FIG. 1. As shown in FIG. 2, the data sampled by the data sampler is stored into a memory 61 via an interface unit 68 and a bus 64. Configuration information and programs for the computer data processor are stored in a Read-Only Memory (ROM) 62. A Random Access Memory (RAM) 63 is used for temporarily storing various data during the operation of a processor 66. In addition, computer programs for data processing are also stored in the memory 61. The internal bus 64 connects the above memory 61, Read Only Memory (ROM) 62, Random Access Memory (RAM) 63, an input device 65, the processor 66, a display device 67, and the interface unit 68.

After an operation command is input by a user via the input device 65, such as a keyboard, a mouse, etc., the instruction code of the computer program instructs the processor 66 to perform a predetermined data processing algorithm. After the result of the data processing is acquired, it will be displayed on the display device 67, such as an LCD display, or output directly in a hardcopy form, such as printing.

Figure 3:
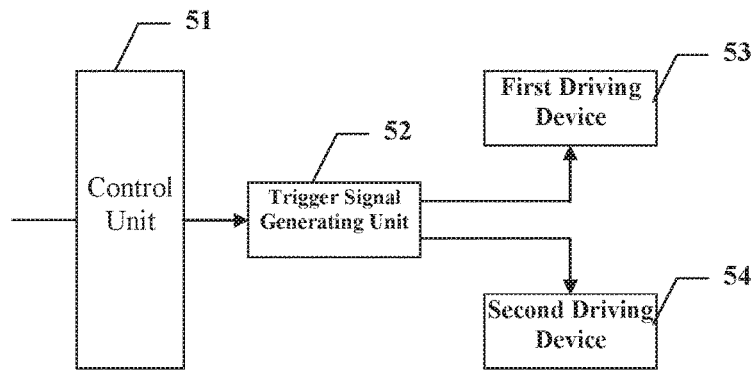
FIG. 3 is a block diagram showing the structure of a controller according to an embodiment of the present disclosure.

FIG. 3 is a block diagram showing the structure of a controller according to an embodiment of the present disclosure. As shown in FIG. 3, the controller 50 comprises: a control unit 51 configured to control the ray source 10, the bearing mechanism 40, and the detection and sampling apparatus 30 based on the instructions from the computer 60; a trigger signal generating unit 52 configured to generate a trigger command to trigger actions of the ray source 10, the detection and sampling apparatus 30, and the bearing mechanism 40 under the control of the control unit; a first driving device 53 configured to drive the bearing mechanism 40 to transfer the luggage to be inspected 70 based on the trigger command which is generated by the trigger signal generating unit 52 under the control of the control unit 51; and a second driving device 54 configured to drive the rack 20 to rotate based on the trigger command which is generated by the trigger signal generating unit 52 under the control of the control unit 51. The projection data acquired by the detection and sampling apparatus 30 is stored in the computer 60 for CT tomographic image reconstruction, thereby acquiring the tomographic image data for the luggage to be inspected 70. After that, the computer 60 acquire a DR image for the luggage to be inspected 70 from at least one viewing angle based on the tomographic image data, for example, by executing software, to be displayed along with the reconstructed three-dimensional image, thereby facilitating a human operator for identifying to perform a security check. According to other embodiments, the above CT imaging system may also be a dual-energy CT system, that is, the X-ray source 10 of the rack 20 may emit two types of rays having high-energy and low-energy, respectively. After the detection and sampling apparatus 30 detects the projection data with different energy levels, the computer data processor 60 may perform a dual-energy CT reconstruction to acquire equivalent atomic number and electron density data for various section layers of the luggage to be inspected 70.

Figure 4:
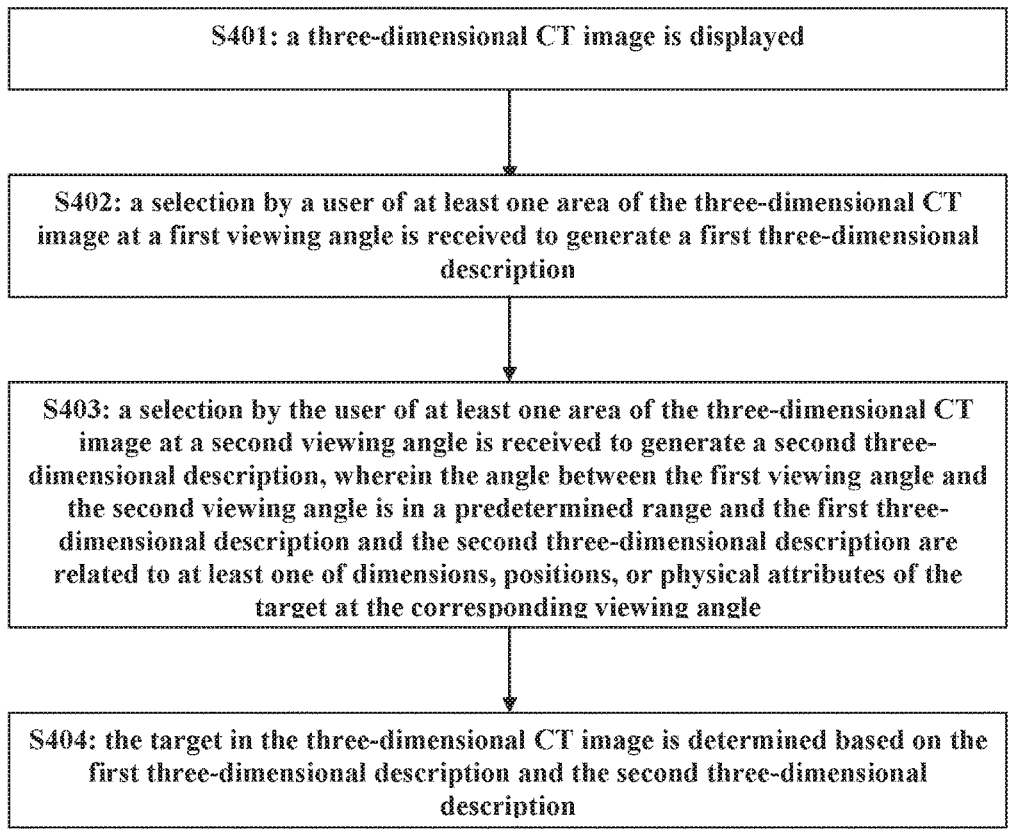
FIG. 4 is a schematic flow chart showing a method for marking a target according to an embodiment of the present disclosure.

FIG. 4 is a schematic flow chart showing a method for marking a target object according to an embodiment of the present disclosure.

As shown in FIG. 4, at step S401, inspection data of an object to be inspected is read to display a three-dimensional image on a display screen.

At step S402, a selection of at least one area of the three-dimensional CT image at a first viewing angle is received from a user by an input device 65, such as a mouse, to generate a first three-dimensional description. For example, the user may operate the input device 65 to mark or circle an area on the image displayed on the screen at the current viewing angle.

At step S403, a selection of at least one area of the three-dimensional CT image at a second viewing angle is received from the user to generate a second three-dimensional description. For example, the user may operate the input device 65 to mark or circle an area on the image displayed on the screen at another viewing angle. The angle between the first viewing angle and the second viewing angle is in a predetermined range and the first three-dimensional description and the second three-dimensional description are related to at least one of dimensions, positions, or physical attributes of the target at the corresponding viewing angle. For example, the angle between these two viewing angles may be in a range from 45 degrees to 135 degrees.

At step S404, the target in the three-dimensional CT image is determined based on the first three-dimensional description and the second three-dimensional description.

Further, with regard to the problem of the prior art, after transparent areas in the data are quickly removed, new incident and exit positions of the projection rays are acquired and recorded as a depth map. Based thereon, a two-dimensional mark is restored to its depth information in the voxel space. A Boolean intersection operation is performed on the two acquired geometries in the image space to finally acquire a marked area in the three-dimensional space.

For example, a front plane depth map and a rear plane depth map at the first viewing angle is acquired, and a searching is performed in the front plane depth map and the rear plane depth map based on the area selected by the user at the first viewing angle, respectively, to generate a first bounding box/data subset as the first three-dimensional description. A three-dimensional drawing result at the second viewing angle is acquired by using the first generated bounding box/data subset as the drawing range, and a front plane depth map and a rear plane depth map at the second viewing angle are acquired. A searching is performed in the front plane depth map and the rear plane depth map based on the area selected by the user at the second viewing angle, respectively, to generate a second bounding box/data subset as the second three-dimensional description. In this way, an intersection operation is performed on the first bounding box/data subset and the second bounding box/data subset in the image space to determine the target.

In other embodiments, the step of acquiring the front plane depth map and the rear pane depth map comprises: a depth test performed in a scenario rendering process and the minimal depth value is recorded to acquire a front plane depth map. A depth test is performed in the scenario rendering process and the maximal depth value is recorded to acquire a rear plane depth map. For example, both of the first bounding box/data subset and the second bounding box/data subset are bounding boxes/data subsets in any arbitrary direction.

In some embodiments, the marked area of the three-dimensional space is merged into and displayed within the CT data.

For example, in some embodiments, transparent areas are first removed to quickly acquire a tightly hierarchical bounding box/data subset for non-transparent area in the data. After that, the above generated hierarchical bounding box/data subset is rendered to acquire the front/rear plane depth maps. These are the incident and exit positions of the adjusted projection rays. Next, a first sampling is performed in a current direction of line of sight, and a searching is performed in the front/rear plane depth maps by using an array of marked points to generate a bounding box, such as an OBB bounding box. After that, based on the above generated OBB bounding box, the projection range of the rays is updated and a second sampling is performed by the user at an orthogonal viewing angle which is reached by an automatic rotation to generate a new OBB bounding box. A Boolean intersection operation is performed on the OBB bounding boxes acquired in previous two steps in the image space to acquire a final marked area. Finally, the suspected area is merged and display in the original data by using a transfer function based on space constraints. By using the marking method of the present disclosure, the transparent areas in the CT data may be removed quickly and accurately to facilitate the user in quickly accomplishing the suspected area marking task in a friendly operation manner.

The above detailed description has already set forth numerous embodiments of the method and apparatus for marking a suspected object in a security check CT system with reference to the diagrams, flow charts, and/or examples. In the case where the diagrams, flow charts, and/or examples comprise one or more functions and/or operations, one skilled in the art should appreciate that each function and/or operation in the diagrams, flow charts, or examples may be implemented by various structures, hardware, software, firmware or any combination thereof either alone and/or in any combination. In an embodiment, several parts of the subject matter described in the embodiments of the present disclosure may be implemented by Application Specific Integrated Circuit (ASIC), Field Programmable Gate Array (FPGA), Digital Signal Processor (DSP), or any other integrated form. However, one skilled in the art should appreciate that some aspects of the embodiment disclosed herein may be partially or wholly implemented in an integrated circuit equivalently, implemented as one or more computer programs running on one or more computers (for example, one or more programs running on one or more computer systems), implemented as one or more programs running on one or more processors (for example, one or more programs running on one or more micro-processors), implemented as firmware, or substantially any combination thereof, and one skilled in the art is capable to design the circuit and/or write software and/or firmware code. Further, one skilled in the art would appreciate that the mechanism of the subject matter of the present disclosure may be distributed in various forms of program products, and the exemplary embodiments of the subject matter of the present disclosure may be applicable irrespective of the specific types of signal carrier media for distribution. Examples of the signal carrier media comprise but not limited to: a recordable medium such as floppy disk, hard drive, compact disk (CD), digital versatile disk (DVD), digital tape, computer memory, etc.; and a transmission medium, such as digital and/or analog communication medium (for example, optical fiber, waveguide, wired communication link, wireless communication link, etc.)

Although the present disclosure is already described with reference to several typical embodiments, it is to be appreciated that the terms used herein are illustrative and exemplary, rather than limiting. Since the present disclosure may be practiced in multiple forms without departing from the spirit or essence, it is to be noted that the above embodiments are not limited to any previously described details and shall be interpreted broadly within the spirit and scope defined by the claims. Therefore, all changes and variations fall into the scope of the claims or their equivalents and shall be embraced by the claims.

We claim:
1. A method for identifying a target in a three-dimensional CT image, the method comprising:
    displaying a three-dimensional CT image generated by a CT apparatus on a physical display apparatus;
    receiving a selection, via one or more physical input devices of a computer system connected to the physical display apparatus, by a user of at least one area of the three-dimensional CT image at a first viewing direction to generate a first three-dimensional description;
    receiving a selection, via the one or more physical input devices of the computer system, by the user of at least one area of the three-dimensional CT image at a second viewing direction to generate a second three-dimensional description, wherein an angle between the first viewing direction and the second viewing direction is in a predetermined range and the first three-dimensional description and the second three-dimensional description are related to at least one of dimensions, positions, or physical attributes of the target at a corresponding viewing direction; and
    identifying the target in the three-dimensional CT image based on the first three-dimensional description and the second three-dimensional description,
    wherein the first three-dimensional description is a first bounding box/data subset and the second three-dimensional description is a second bounding box/data subset.

2. The method according to claim 1, wherein the generating the first three-dimensional description further comprises:
    acquiring a front plane depth map and a rear plane depth map at the first viewing direction, and
    searching in the front plane depth map and the rear plane depth map based on the at least one area selected by the user at the first viewing direction, respectively, to generate the first bounding box/data subset;
    wherein the generating the second three-dimensional description further comprises:
    acquiring a three-dimensional drawing result at the second viewing direction by using the first generated bounding box/data subset as the drawing range,
    acquiring a front plane depth map and a rear plane depth map at the second viewing direction, and
    searching in the front plane depth map and the rear plane depth map based on the at least one area selected by the user at the second viewing direction, respectively, to generate the second bounding box/data subset;
    wherein the identifying the target in the three-dimensional CT image comprises:
    performing an intersection operation on the first bounding box/data subset and the second bounding box/data subset in an image space to identify the target.

3. The method according to claim 2, wherein the acquiring the front plane depth map and the rear plane depth map comprises:
    performing a depth test in a scenario rendering process and recording the minimal depth value to acquire a front plane depth map; and
    performing a depth test in the scenario rendering process and recording the maximal depth value to acquire a rear plane depth map.

4. The method according to claim 2, wherein a marked area of the three-dimensional space acquired from performing the intersection operation is merged into and displayed within the CT data.

5. The method according to claim 1, wherein both the first bounding box/data subset and the second bounding box/data subset are bounding boxes/data subsets in any arbitrary direction.

6. The method according to claim 1, wherein the predetermined range is specifically a range from 45 degrees to 135 degrees.

7. A security check CT system, comprising:
a CT scanning device configured to acquire inspection data for an object to be inspected;
a memory configured to store the inspection data;
a display device configured to display a three-dimensional CT image for the object to be inspected;
an input device configured to input a selection by a user of at least one area of the three-dimensional CT image at a first viewing direction, and to input a selection by the user of at least one area of the three-dimensional CT image at a second viewing direction, wherein an angle between the first viewing direction and the second viewing direction is in a predetermined range; and
a data processor configured to generate a first three-dimensional description based on the selection at the first viewing direction, generate a second three-dimensional description based on the selection at the second viewing direction, and identify the target in the three-dimensional CT image based on the first three-dimensional description and the second three-dimensional description,
wherein the first three-dimensional description and the second three-dimensional description are related to at least one of the dimensions, positions or physical attributes of the target at a corresponding viewing direction, and
wherein the first three-dimensional description is a first bounding box/data subset and the second three-dimensional description is a second bounding box/data subset.

8. The security check system according to claim 7, wherein the data processor is configured to:
acquire a front plane depth map and a rear plane depth map at the first viewing direction, and search in the front plane depth map and the rear plane depth map based on the at least one area selected by the user at the first viewing direction, respectively, to generate the first bounding box/data subset;
acquire a three-dimensional drawing result at the second viewing direction by using the first generated bounding box/data subset as the drawing range, acquire a front plane depth map and a rear plane depth map at the second viewing direction, and search in the front plane depth map and the rear plane depth map based on the at least one area selected by the user at the second viewing direction, respectively, to generate the second bounding box/data subset; and
perform an intersection operation on the first bounding box/data subset and the second bounding box/data subset in an image space to identify the target.

9. The security check system according to claim 8, wherein the data processor is configured to:
perform a depth test in a scenario rendering process and record the minimal depth value to acquire a front plane depth map; and
perform a depth test in the scenario rendering process and record the maximal depth value to acquire a rear plane depth map.

10. The security check system according to claim 7, wherein both the first bounding box/data subset and the second bounding box/data subset are bounding boxes/data subsets in any arbitrary direction.

11. The security check system according to claim 7, wherein a marked area of the three-dimensional space acquired from performance of the intersection operation is merged into and displayed within the CT data.

12. The security check system according to claim 7, wherein the predetermined range is specifically a range from 45 degrees to 135 degrees.

13. A non-transitory computer-readable medium comprising instructions configured to cause a processor system to at least:
cause display of a three-dimensional CT image produced by a CT apparatus on a physical display apparatus;
receive, via one or more physical input devices of a computer system connected to the physical display apparatus, a selection by a user of at least one area of the three-dimensional CT image at a first viewing direction to generate a first three-dimensional description;
receive, via the one or more physical input devices of the computer system, a selection by the user of at least one area of the three-dimensional CT image at a second viewing direction to generate a second three-dimensional description, wherein an angle between the first viewing direction and the second viewing direction is in a predetermined range and the first three-dimensional description and the second three-dimensional description are related to at least one of dimensions, positions, or physical attributes of the target at the corresponding viewing direction; and
identify the target in the three-dimensional CT image based on the first three-dimensional description and the second three-dimensional description,
wherein the first three-dimensional description is a first bounding box/data subset and the second three-dimensional description is a second bounding box/data subset.

14. The non-transitory computer-readable medium according to claim 13, wherein the instructions configured to cause a processor system to generate the first three-dimensional description are further configured to:
acquire a front plane depth map and a rear plane depth map at the first viewing direction, and search in the front plane depth map and the rear plane depth map based on the at least one area selected by the user at the first viewing direction, respectively, to generate the first bounding box/data subset;
wherein the instructions configured to cause a processor system to generate the second three-dimensional description are further configured to:
acquire a three-dimensional drawing result at the second viewing direction by using the first generated bounding box/data subset as the drawing range, acquire a front plane depth map and a rear plane depth map at the second viewing direction, and search in the front plane depth map and the rear plane depth map based on the at least one area selected by the user at the second viewing direction, respectively, to generate a second bounding box/data subset as the second three-dimensional description;

wherein the instructions configured to cause a processor system to identify the target in the three-dimensional CT image are further configured to:
perform an intersection operation on the first bounding box/data subset and the second bounding box/data subset in an image space to identify the target.

15. The non-transitory computer-readable medium according to claim 14, wherein the instructions configured to cause a processor system to acquire the front plane depth map and the rear plane depth map are further configured to:
perform a depth test in a scenario rendering process and record the minimal depth value to acquire a front plane depth map; and
perform a depth test in the scenario rendering process and record the maximal depth value to acquire a rear plane depth map.

16. The non-transitory computer-readable medium according to claim 14, wherein a marked area of the three-dimensional space acquired from performance of the intersection operation is merged into and displayed within the CT data.

17. The non-transitory computer-readable medium according to claim 13, wherein both the first bounding box/data subset and the second bounding box/data subset are bounding boxes/data subsets in any arbitrary direction.

18. The non-transitory computer-readable medium according to claim 13, wherein the predetermined range is specifically a range from 45 degrees to 135 degrees.

* * * * *